United States Patent [19]

Shroot et al.

[11] Patent Number: 5,196,577
[45] Date of Patent: Mar. 23, 1993

[54] COMPOUND MARKED WITH TRITIUM, ITS PREPARATION AND ITS USE IN PARTICULAR IN THE DETERMINATION OF THE AFFINITY OF RETINOIDS FOR THEIR NUCLEAR RECEPTORS AND THEIR CYTOSOLIC BINDING PROTEIN

[75] Inventors: Braham Shroot; Yves M. Darmon, both of Antibes; Philippe Nedoncelle; Claude Martin, both of Grasse, all of France

[73] Assignee: Centre International de Recherches Dermatologiques, Valbonne, France

[21] Appl. No.: 400,537

[22] Filed: Aug. 31, 1989

[30] Foreign Application Priority Data

Sep. 1, 1988 [FR] France ............................ 88 11469

[51] Int. Cl.$^5$ ...................... C07C 63/49; A61K 49/02; C07B 59/00
[52] U.S. Cl. ................................. 562/490; 424/1.1; 435/7.1; 435/7.23; 435/968
[58] Field of Search ............... 424/1.1; 562/490, 492; 514/569

[56] References Cited

FOREIGN PATENT DOCUMENTS 2194535 3/1988 United Kingdom .

OTHER PUBLICATIONS

Dawson et al., *J. Med. Chem.*, vol. 32, pp. 1504–1517, (Jul. 1989).
Dawson et al., *J. Labelled Cmpds. Radiopharm.*, vol. 28, No. 1, pp. 89–98.

*Primary Examiner*—Robert L. Stoll
*Assistant Examiner*—John M. Covert
*Attorney, Agent, or Firm*—Cushman, Darby & Cushman

[57] ABSTRACT

4-(5,6,7,8-tetrahydro-5,5,8,8-tetramethyl-2-anthracenyl) benzoic acid marked with tritium is used as a radioactive marker in the titration of nuclear receptors and CRABP, in the measurement of the affinity of retinoids for nuclear receptors and CRABP, in the titration of known retinoids, the characterization of antibodies directed against 4-(5,6,7,8-tetrahydro-5,5,8,8-tetramethyl-2-anthracenyl) benzoic acid, and in the study of the distribution and metabolism of said benzoic acid derivative.

2 Claims, 10 Drawing Sheets

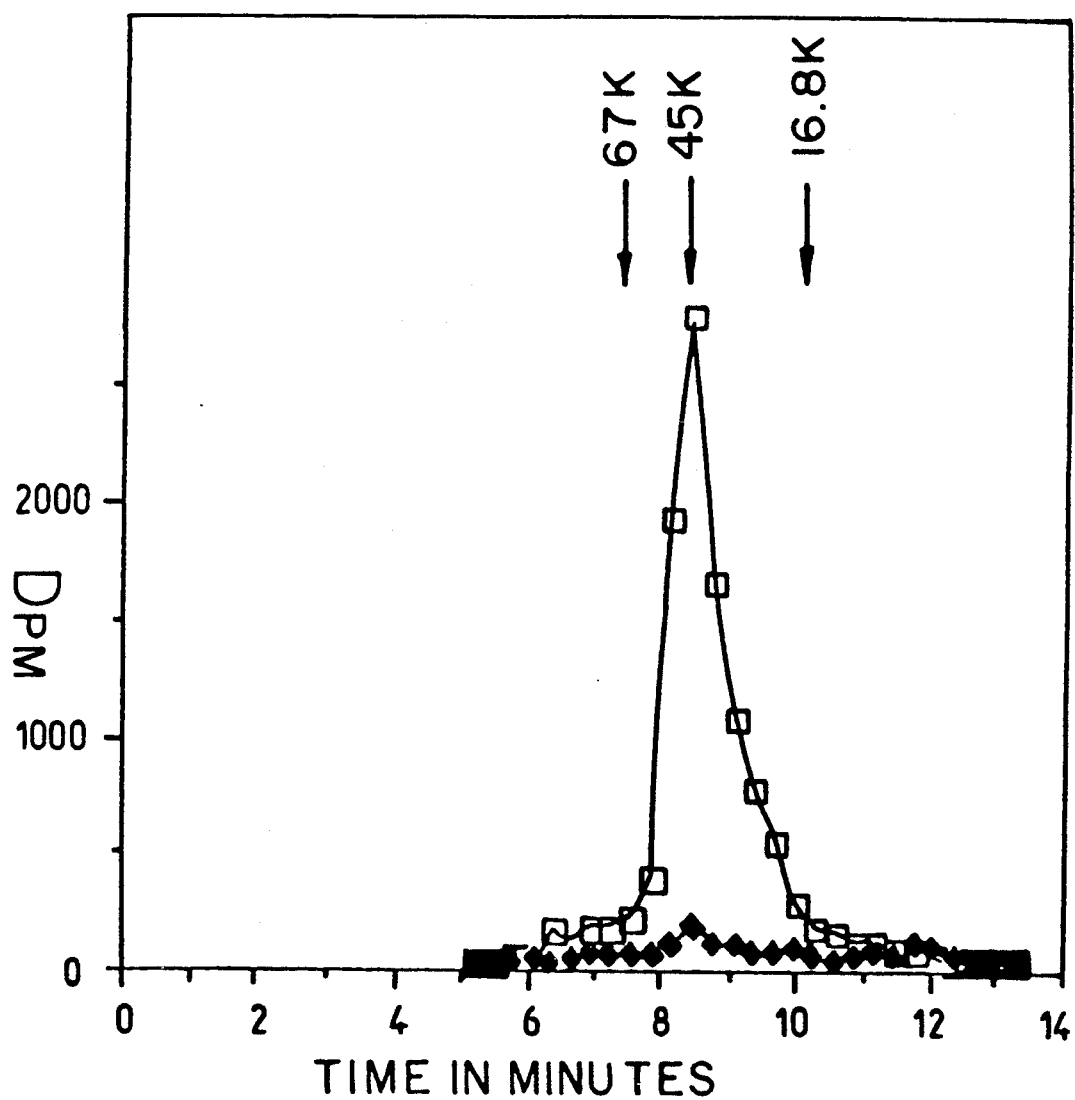

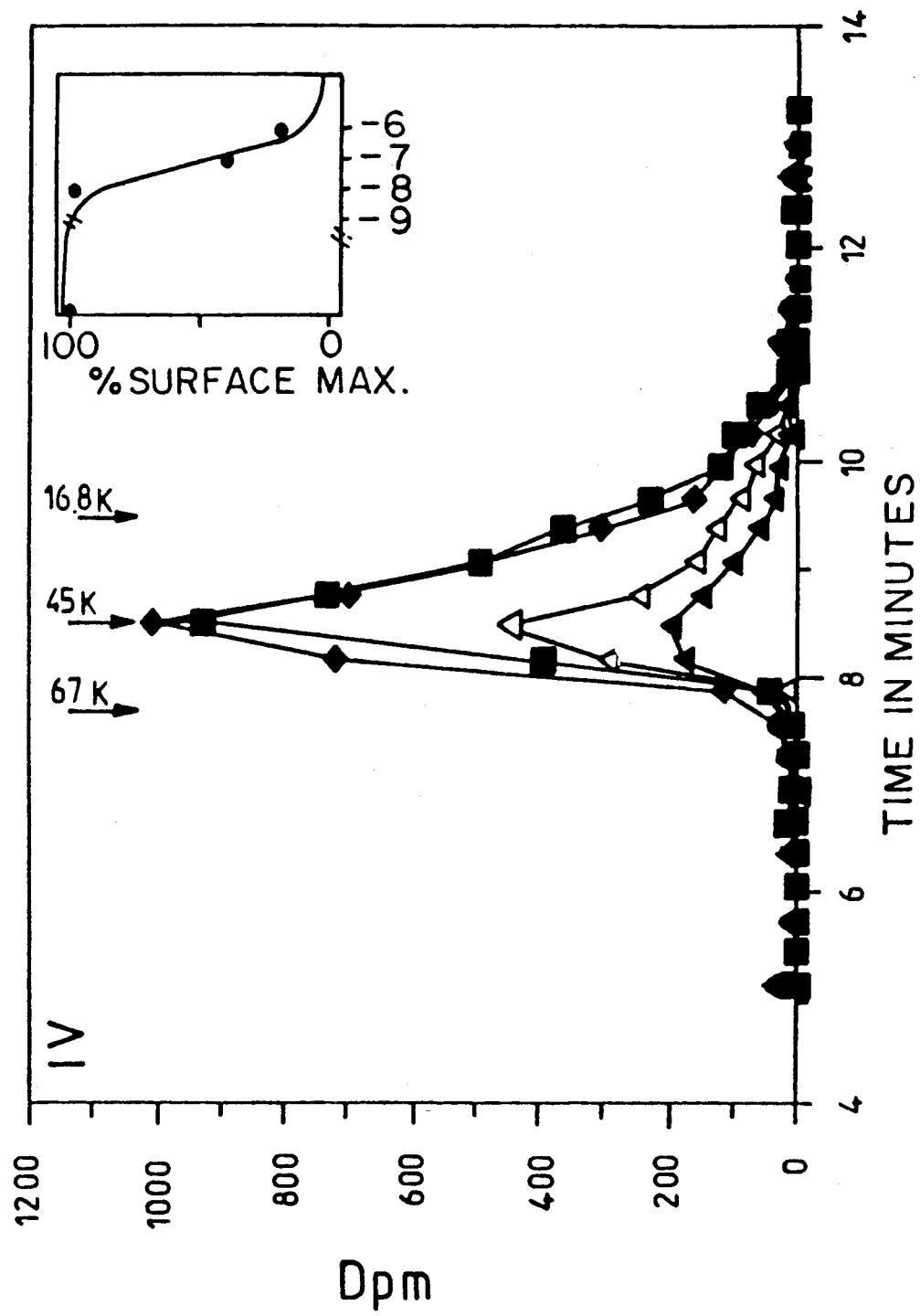

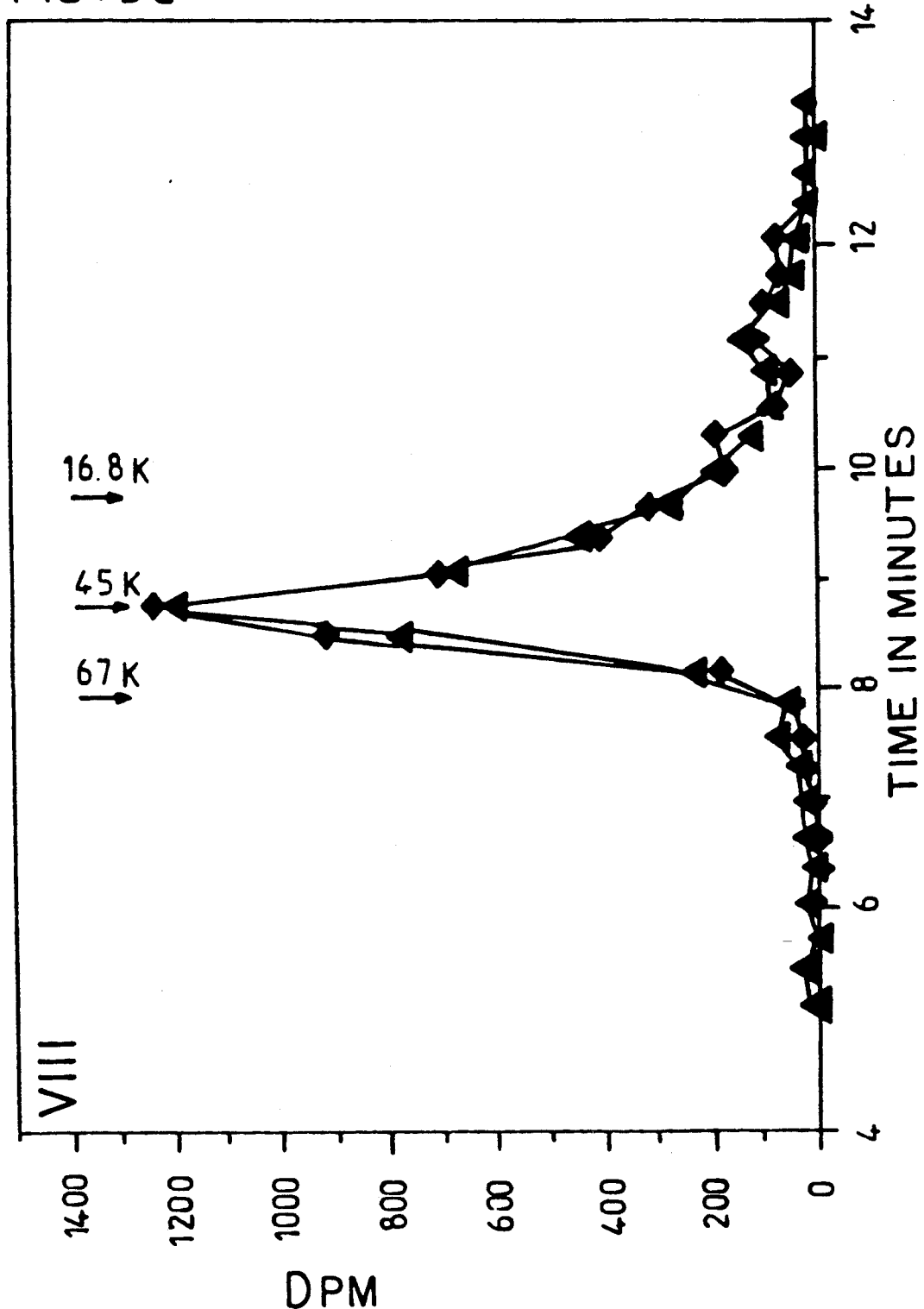

RA : RETINOIC ACID
Rol : RETINOL

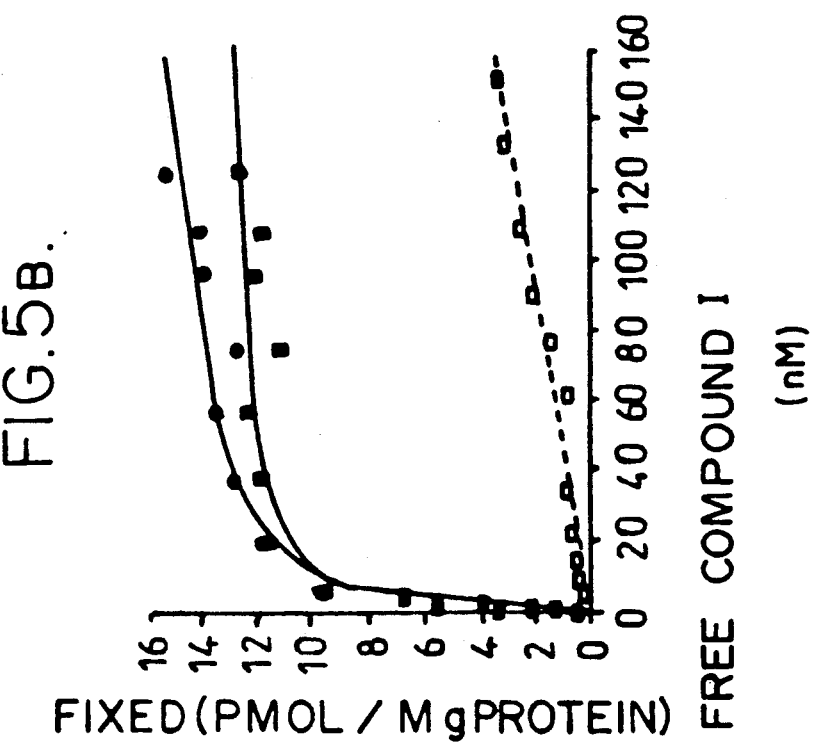
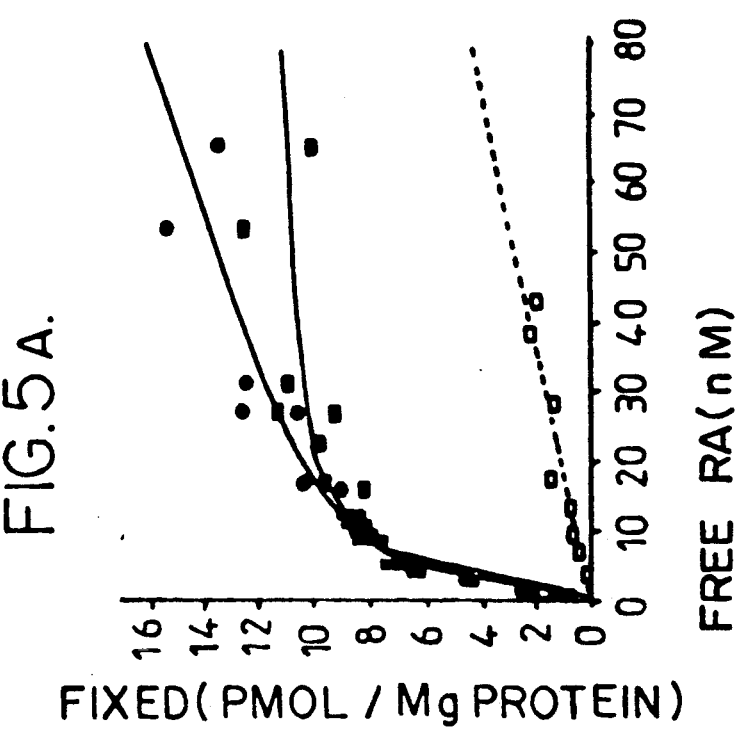

COMPOUND MARKED WITH TRITIUM, ITS PREPARATION AND ITS USE IN PARTICULAR IN THE DETERMINATION OF THE AFFINITY OF RETINOIDS FOR THEIR NUCLEAR RECEPTORS AND THEIR CYTOSOLIC BINDING PROTEIN

The present invention relates to a new compound, marked with tritium, which is related to retinoids, to its preparation and to its use, in particular, in the determination of the affinity of retinoids for their nuclear receptors and their cytosolic binding protein and/or in the determination of the content of nuclear receptor and cytosolic binding protein cells.

It is known that retinoids constitute a known class of compounds which act, in particular, on the proliferation and differentiation of numerous types of cells; see, for example, B. A. Pawson et al, Journal of Medicinal Chemistry, Vol. 25, No. 11, pages 1269-1277 (1982).

Retinoids have been used, in particular, in the treatment of various dermatological disorders in which an irregularity of the mechanisms for control of the proliferation and differentiation of the epidermal cells is involved; see, for example, the work "Update: Dermatology in General Medicine", edited by Thomas B. Fitzpatrick et al (MacGraw-Hill Book Company), published in 1983, and particularly the chapter by D. B. Windhorst et al, The Retinoids, pages 226-237.

The method of action of retinoids is similar to that of steroids and other effectors interacting with nuclear receptors (Chytil & Ong, 1979). Retinoic acid nuclear receptors (RARs) have been isolated (Daly & Redfern, 1987) and the corresponding complementary DNAs have been cloned and sequenced (Petkovich et al, 1987; Brand et al, 1988). To date, three receptors have been described in man, RARa (462 residues), RARb (448 residues) and RAR (458 residues). In addition, it has been shown that there exists in cytosol a binding protein, known as CRABP (cellular retinoic acid binding protein), but its role is little known.

The determination of the affinity of a retinoid for the RARs comprises a particularly interesting method of potential biological evaluation of said retinoid. The determination of the affinity for the CRABP provides an additional element of evaluation.

Several experimental methods enable the determination of the affinity of a ligand for its receptors or binding proteins. In particular, a direct method can be used if the ligand under consideration is radioactively marked, or even by competition with a radioactive ligand if the ligand under consideration is not radioactively marked.

A good radioactive ligand must, on the one hand, have a high affinity for its receptors and binding proteins and, on the other hand, have low fixing on any other molecule. In addition, it must be sufficiently stable to be useful in practice.

In the case of retinoid acids, the radioactive ligand generally used is most often tritiated retinoic acid, either in the 2-position (J. Labelled Compounds and Radiopharmaceuticals XVIII, p. 1099 (1980)) or in the 4-position (German Patent Application No. 3,142,975).

Retinoic acid certainly has an excellent affinity for RARs and CRABP, with low non-specific fixing, but the molecule has the disadvantage of becoming rapidly degraded, by radiolysis, oxidation and photolysis.

It has now been discovered that tritiated 4-(5,6,7,8-tetrahydro-5,5,8,8-tetramethyl-2-anthracenyl) benzoic acid constitutes a new radioactive ligand which has an excellent affinity for RARs and CRABP, with low non-specific fixing. In addition, this new ligand is very stable and can be obtained with high specific activity, which makes it particularly useful for the measurement of the affinity of retinoids for RARs and CRABP.

The present invention therefore relates to 4-(5,6,7,8-tetrahydro-5,5,8,8-tetramethyl-2-anthracenyl) benzoic acid marked with tritium.

In particular, the present invention relates to a new radioactive ligand, as defined above, having a specific activity of greater than 30 Ci/mmole and preferably at least equal to 50 Ci/mmole, or approximately 1875 GBq/mmole.

The present invention also relates to a method for the preparation of the new radioactive ligand, such as defined above. This method is principally characterized by the fact that a multihalogenated alkyl ester of 4-(5,6,7,8-tetrahydro-5,5,8,8-tetramethyl-2-anthracenyl) benzoic acid is prepared Depending on the number of equivalents of the halogenation agent selected, up to five atoms of halogen can be added. The halogenated alkyl ester is then submitted to the action of a tritiated reducing agent.

The reducing agent is, for example, tritium which is used in the presence of 10% palladium on carbon, and triethylamine.

The reduction of the halogenated derivative is preferably carried out at room temperature and under ambient pressure, for example, at 15°-30° C. under a pressure of 1 bar (which is approximately $10^5$ Pa).

The alkyl ester is then saponified in a methanol medium in the presence of soda.

The halogenated derivative used as the starting product is preferably the brominated derivative. The alkyl ester used is preferably the ethyl ester.

The halogenated alkyl ester of 4-(5,6,7,8-tetrahydro-2-5,5,8,8-tetramethyl-2-anthracenyl) benzoic acid can itself be prepared from the alkyl ester of 4-(5,6,7,8-tetrahydro-5,5,8,8-tetramethyl-2-anthracenyl) benzoic acid by the action of a halogenation agent (in particular a bromination agent). For example, the brominated derivative can be obtained by the action of bromine in acetic acid at room temperature and under a nitrogen atmosphere.

4-(5,6,7,8-tetrahydro-5,5,8,8-tetramethyl-2-anthracenyl) benzoic acid is a known product (hereinafter called "compound I") and can be obtained using the method described, for example, in European Patent Application No. 86.401671 (210.929) filed Jul. 25, 1986.

The radioactive ligand of the present invention can also be obtained starting from the alkyl ester of 4-(5,6,7,8-tetrahydro-5,5,8,8-tetramethyl-2-anthracenyl) benzoic acid by isotopic exchange with tritiated water in the presence of platinum and acetic acid at a temperature preferably ranging from 60° to 150° C. In this case, the isotopic exchange is preferably carried out with the aromatic protons of the ligand.

The present invention also relates to the use of tritiated 4-(5,6,7,8-tetrahydro-5,5,8,8-tetramethyl-2-anthracenyl) benzoic acid as a radioactive marker, in particular in the determination of the affinity, of the presence or of the content of retinoids and/or in the quantification of the RARs and CRABP of said retinoids.

For example, the radioactive marker of the invention can be used during the purification of RARs and CRABP using conventional methods of exclusion chromatography under low or high pressure; it is sufficient to add to the cells (in the case of RARs) or to the tissue extract (in the case of CRABP), used as starting products, a determined quantity of the radioactive ligand. The RARs and CRABP are thus marked and their presence o their absence in a given fraction can easily be marked.

The knowledge of the fixing curves on the RARs or CRABP also enables the use of the marker of the invention in the quantification of endogenous RARs or those obtained by transfection methods, or in the quantification of CRABP.

The present invention also relates to the use of tritiated compound I:

as a radioactive marker to locate, titrate or mark the nuclear receptors of retinoic acid:

as a radioactlve marker to measure the affinity of the retinoids for the RARs (competition experiments) and thus provide an estimation of their biological activity;

as a radioactive marker to locate, titrate or mark CRABP; or to titrate a known retinoid by competition for fixing on CRABP;

as a radioactive marker to measure the affinity of retinoids for CRABP.

The radioactive marker of the present invention can also be used in the characterization of antibodies against compound I, with these antibodies (obtained using conventional methods for obtaining antihapten antibodies) themselves being usable in the determination of the quantity of product I fixed or unfixed on the RARs and/or the CRABP. The marked antibodies are used to carry out a radioimmunodosage.

The radioactive marker of the present invention can also be used in the study of the mechanism for intracellular action and of the general mechanism of compound I in vivo and in the cells and cellular extracts, and also for studying the in vivo as well as cellular and subcellular distribution of said compound and of retinoids in general.

In the Drawings

FIGS. 1A and 1B represent the high performance exclusion chromatography (HPSEC) profile in the detection of retinoic acid nuclear receptors, respectively;

FIGS. 3a, 3b, 3c and 3d represent the HPSEC profiles of the affinity of compound I, compound IV, retinoic acid and compound VIII for RARs, respectively;

FIGS. 5A and 5B illustrate the fixing of retinoic acid and compounds I, respectively on CRABP.

Figure 1A:
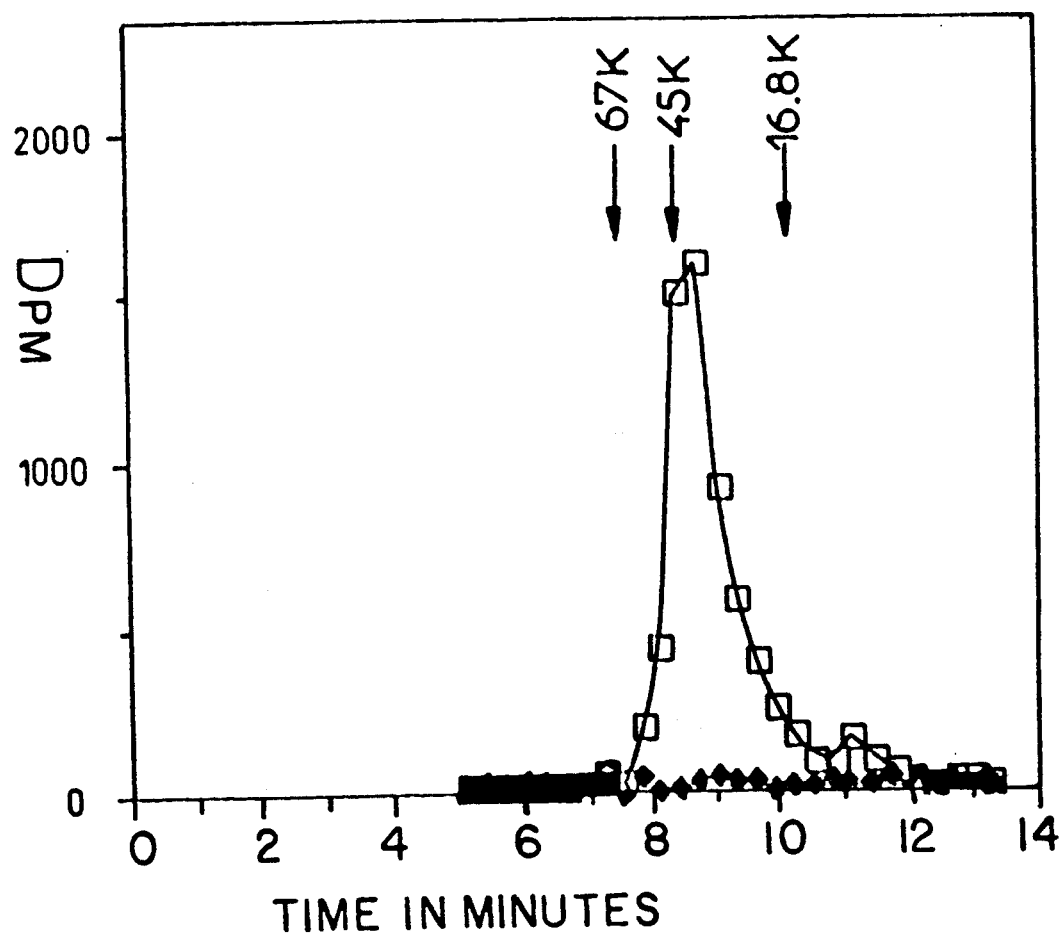

The following example illustrates the invention without, however, limiting it.

EXAMPLE 1

4-(5,6,7,8-tetrahydro-5,5,8,8-tetramethyl-2-anthracenyl) benzoic acid marked with tritium:

a) The ethyl ester corresponding to the cited acid (250 mg; 0.644 mmole) was placed in solution in 25 ml of acetic acid under a nitrogen atmosphere. 1 ml of a solution of bromine in acetic acid (230 mg of bromine per ml, which is 2.2 equivalents) was added.

The mixture was stirred for 4 hours at room temperature, poured into 100 ml of water and then extracted with dichloromethane (100 ml).

The organic phase was separated, washed with water and then using a saturated solution of sodium bicarbonate and finally sodium thiosulfate.

It was dried on anhydrous magnesium sulfate, and the solvent was then evaporated under reduced pressure.

350 mg of a light yellow solid were obtained, corresponding to a brominated product according to its mass spectrum.

b) The brominated compound obtained was then tritiated. 19.3 mg of brominated precursor were solubilized in a mixture composed of 2 ml of ethanol and 1 ml of THF.

17 $\mu$l of triethylamine and 14 mg of 10% palladium on carbon were added.

The reaction medium was stirred for 2 hours under a tritium atmosphere (1 atmosphere). The catalyst was then filtered, and the labiles were removed twice using 10 ml of a mixture composed of 50% ethanol and 50% acetonitrile.

The product was dissolved with 100 ml of ethanol.

1,500 mCi of tritiated ethyl ester were obtained.

c) The above tritiated product (1.5 Ci) was solubilized in 5 ml of methanol, 1 ml of 5N soda was added and the resulting mixture was heated to reflux for 2 hours, cooled, acidified with 2 ml of 6N hydrochloric acid, and then extracted with 50 ml of ethyl ether.

The ether phase was decanted, washed with water, dried on anhydrous magnesium sulfate, and the solvents evaporated under reduced pressure. The residue obtained was dissolved in a minimum of dichloromethane and purified by high performance liquid chromatography (eluent: dichloromethane/ methanol 9:1).

The final product was dissolved in 100 ml of methanol. Its purity was verified by thin layer chromatography (silica; eluent as above). A single spot was apparent under UV irradiation (254 and 66 nm) and during beta counting.

Using HPLC (inverse phase, ZORBAX ODS column, eluent: acetonitrile/water/trifluoroacetic acid 95:4.9:0:1), a single peak was detected using UV (254 nm) and using beta detection (continuous liquid scintillation).

The specific activity determined by UV spectrophotometry and then beta counting was 52.8 Ci/mmole.

The total activity obtained, measured by liquid scintillator counting, was 52.8 Ci/mmole.

Characteristics of the fixing of the compound of example 1 on the nuclear receptors RARs Cultures of F9 cells of murin embryonic carcinoma (normally four 90 mm dishes containing in total $2-4 \times 10^7$ cells per incubation condition) were washed once with PBS (saline phosphate buffer) and incubated for 3 hours in a medium, without serum, supplemented with the marked retinoid in the absence or the presence of a cold retinoid homolog or heterolog (to verify the specificity and for comparison experiments). The cells were then detached with a trypsin EDTA mixture and numbered with a Burker hemocytometer. The nucleosol containing RARs was extracted from the purified nuclei using the method described by Daly and Redfern (1987) (that is, after treatment using DNAase and NaCl 0.6M), and analyzed using high performance exclusion chromatography (HPSEC). 50 $\mu$l of marked extract were injected on a $9 \times 250$ mm GF250 column (Dupont de Nemours). The elution was carried out in a buffer 0.3M $KH_2PO_4$ pH 7.8 at a rate of 1 ml/min. The protein content was followed by measuring the optical density at 280 nm. 28 fractions of 0.3 ml each were collected and counted in Picofluor (Packard) scintillating agent. For each retinoid concentration, the number of bonded molecules was determined using the surface of the radioactivity peak and the calculated concentration of demi-saturation (C50). In the competition experiments, 50% inhibitor concentrations (IC50) were calculated, with the compound of example I being used at a concentration of $2.10^{-9}$M. The molecular weight calibration of the column was carried out using human albumin (67 kDa), ovalbumin (45 kDa) and myoglobin (16.8 kDa). The dose-response curves and the competition curves were analyzed on a computer through non-linear regression using the various forms of the Clark equation.

FIG. 1 represents the HPSEC profile in the detection of retinoic acid nuclear receptors (RARs) in a fraction of approximately 45 kDa in the nucleosol of $F^9$ cells, and enabled the study of the specificity of fixing.

The $F^9$ cells were incubated with 200 nM of tritiated retinoic acid (A) or the tritiated compound of example 1 (B) in the absence (□-□) or presence (♦-♦) of 20,000 nM of cold homolog ligand.

When the above-describe method is used and the F9 cells are incubated with the compound of example 1 at a concentration of 200 nM, a single radioactivity peak is observed in the nuclear extract (FIG. 1B). The molecular weight corresponding to the average fraction of the peak is approximately 45 kDa, a number close to the molecular weight of human RARs, as has been calculated from the sequence of their DNAc (Petkovich et al, 1987; Brand et al, 1988), and is compatible with the 4S sedimentation coefficient of murin receptors (Daly & Redfer, 1987). The fixing is specific since it is abolished when the cells are coincubated with an excess of 100 times of the cold compound I (FIG. 1B). There is no CRABP in the nucleosoilc extract of F9, as already underlined by Daly and Redfern (1987).

On the other hand, by transfection of cellular stock not containing retinoid receptors with expression vectors coding separately for each retinoid receptor, it is possible to isolate cellular extracts containing each receptor and to carry out a binding test using the protocol described above. In this manner, the affinity of the compound of example I can be determined for each retinoid receptor.

Comparison with the fixing of tritiated retinoic acid on the nuclear receptors RARs FIG. 1A shows the HPSEC profile obtained after treatment of the cells with 200 nM of tritiated retinoic acid (specific activity=52.5 Ci/mmole). It can be noted that the radioactive peak elutes at the same position as with the compound of example 1. On the other hand, the peak is not observed when the cells have been coincubated with 20000 nM of cold retinoic acid.

Figure 2A:
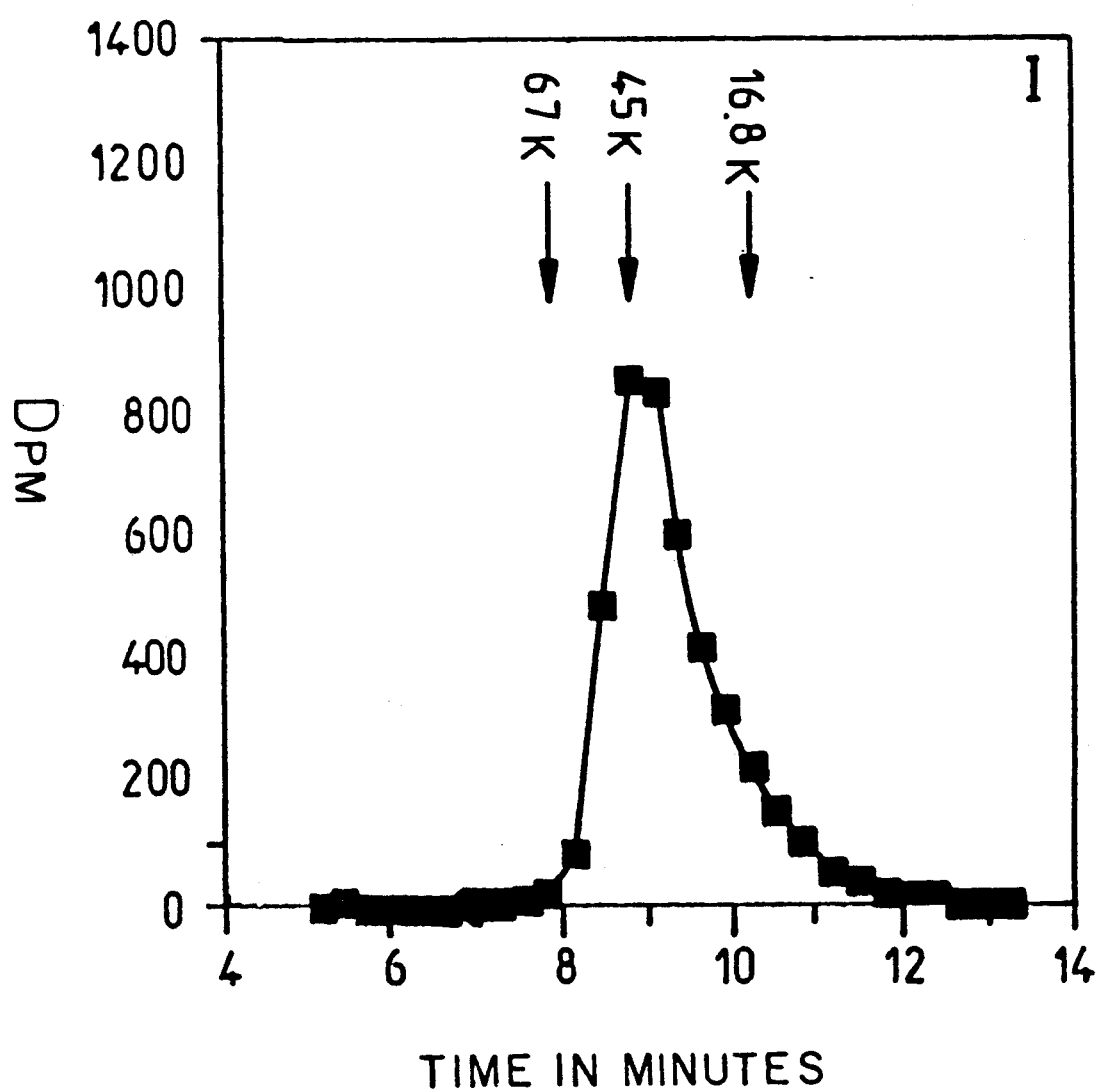
FIGS. 2A and 2B represent the HPSEC profiles in the detection of the fixing of the compound of Example 1 and retinoic acid on RARs, respectively.
Figure 2B:
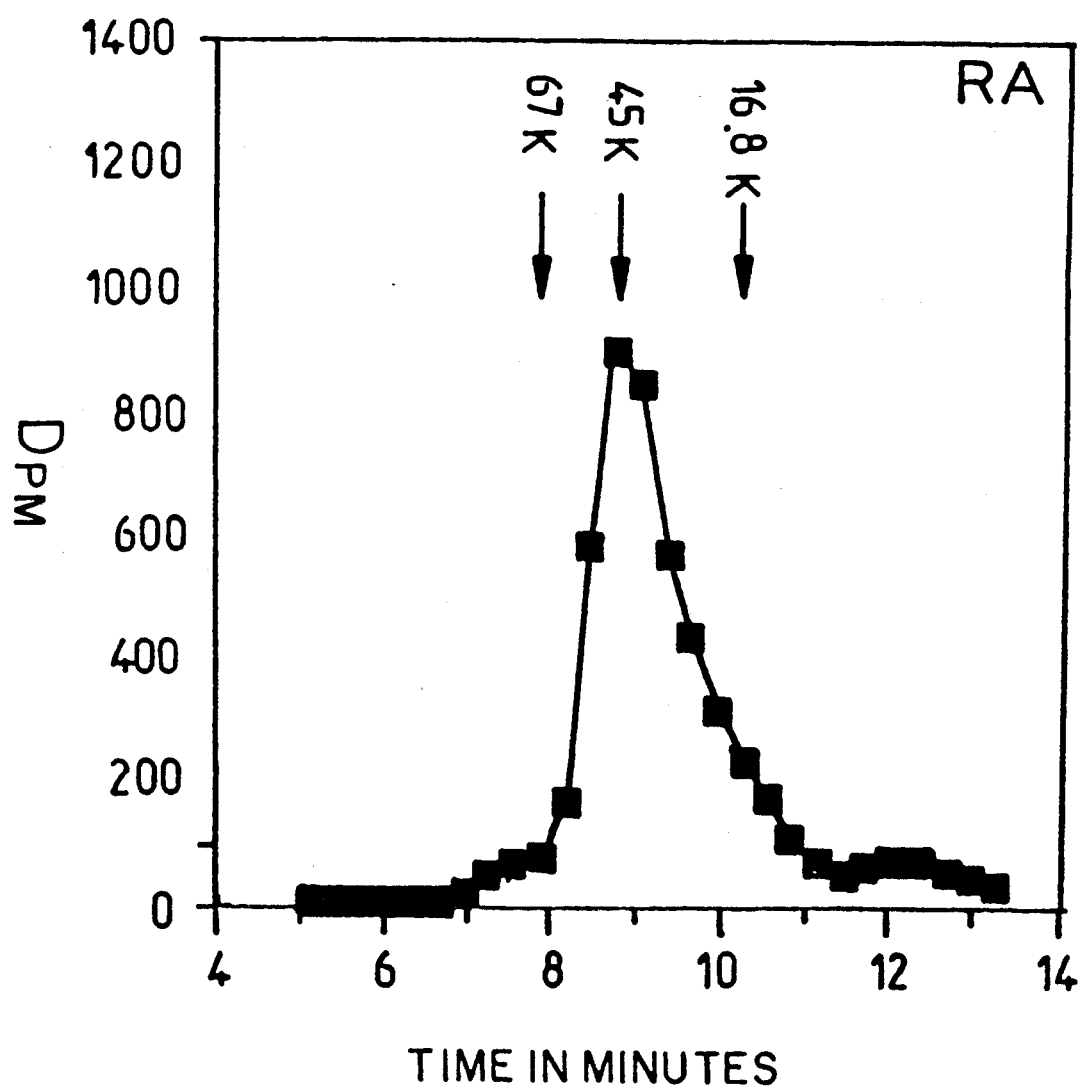

FIG. 2 gives the results relative to the fixing of retinoic acid and the compound of example 1 on the RARs. The two compounds were used at a concentration of 200 nM. The quantity of ligand bonded to the RARs is expressed in molecules per cell.

In the HPSEC results are standardized as a function of the number of cells, that is, by expressing them by molecules of ligand fixed to the RARs per cell, the compound of example 1 and retinoic acid give a peak with the same surface corresponding to approximately 4,000 molecules per cell (FIG. 2).

To determine the concentration of the compound of example 1 giving 50% saturation of the RARs (C50), a saturation curve has been traced expressing the surface of the radioactive peak as a function of varied concentrations of the compound of example 1. The C50 is between 0.5 and 2 nM.

Determination of the affinity of the retinoids for the RARs by competition with the tritiated compound of example 1.

Figure 3A:
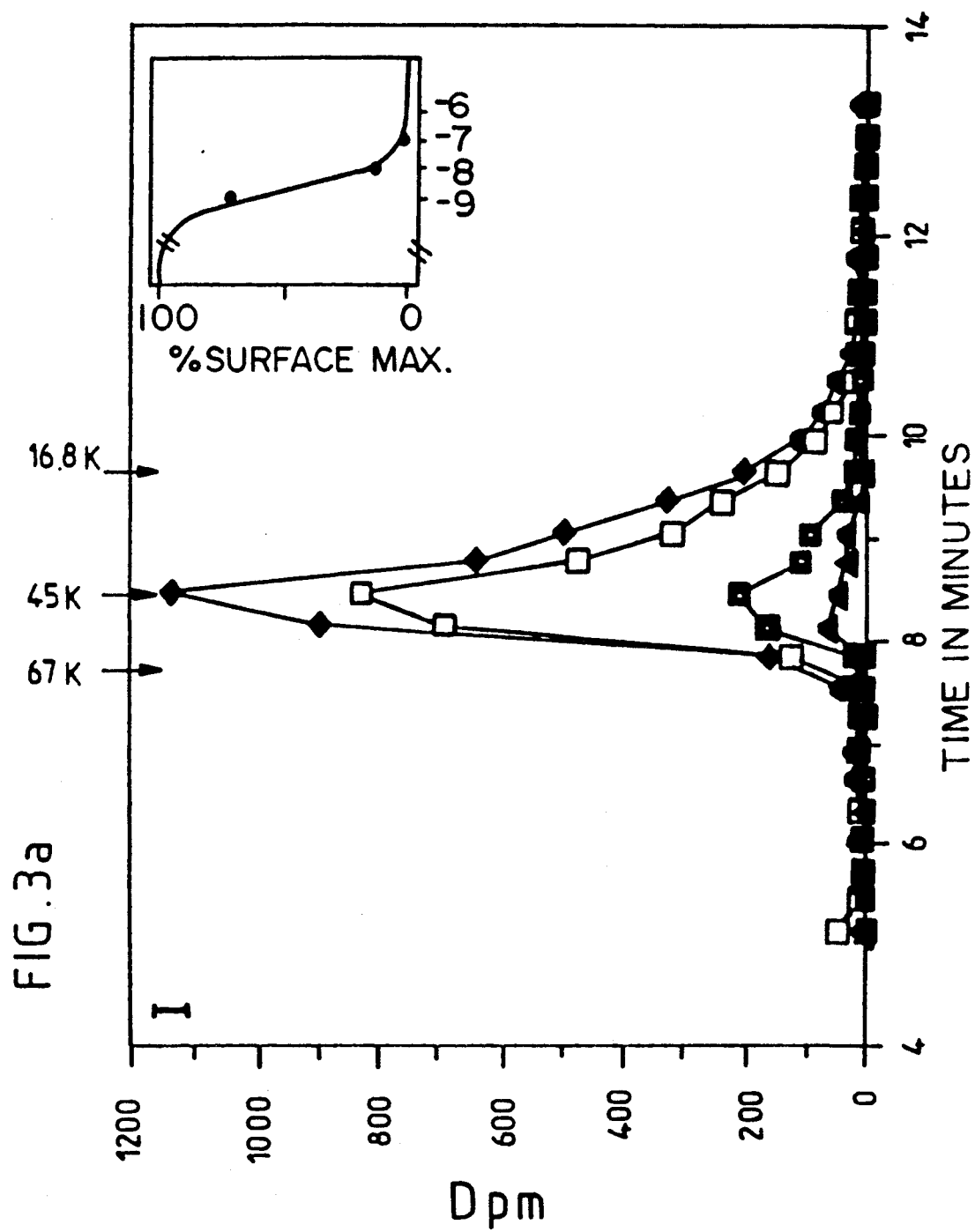
Figure 3C:
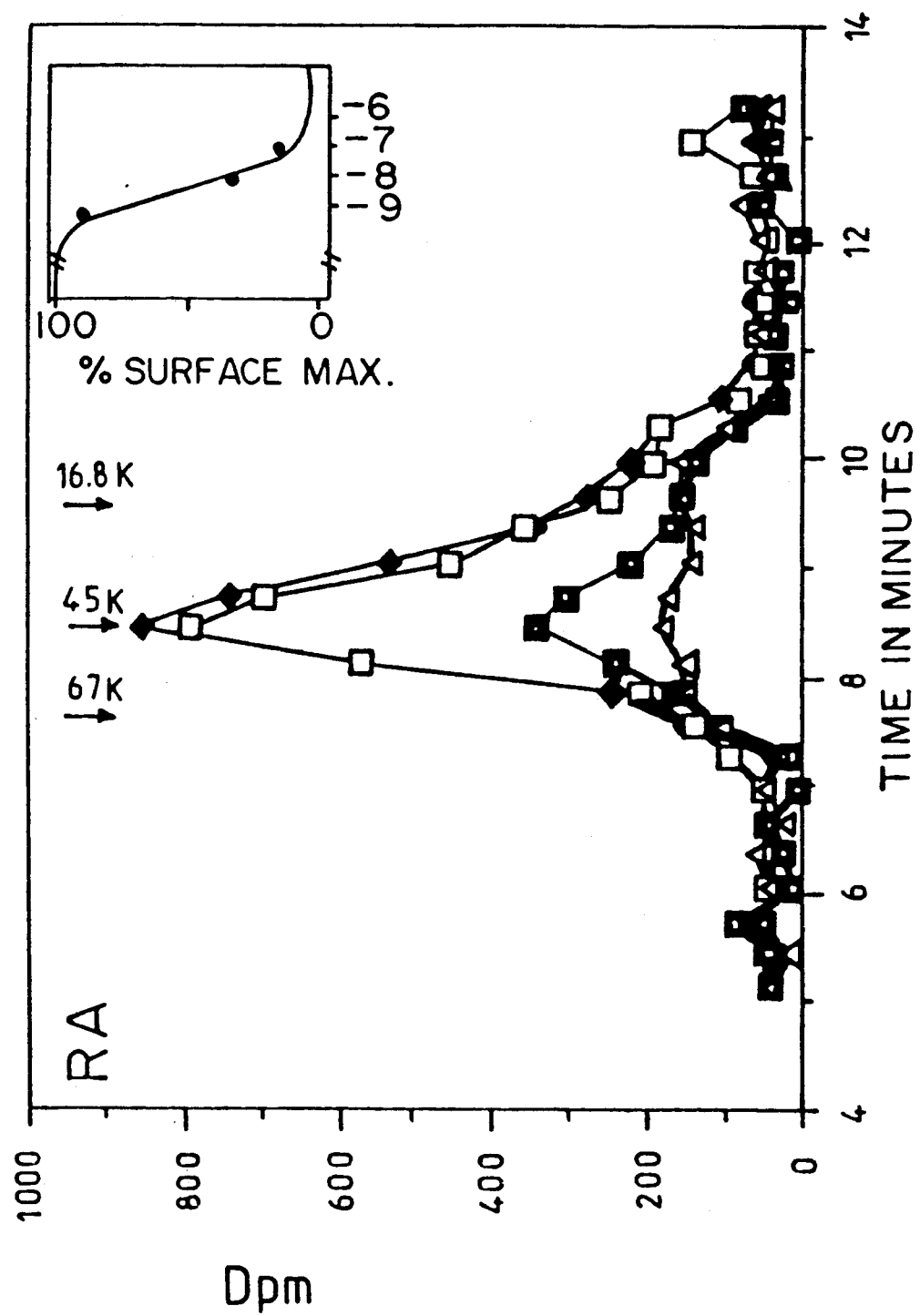

In view of its stability and its excellent affinity for the RARs, the compound of example 1 in principle enables the determination by competition of the affinity of no matter which retinoid for the RARs. FIG. 3 shows the comparative experiments carried out with a fixed concentration of 2 nM of the compound of example 1 and variable concentrations of other retinoids ($10^{-6}$M to $10^{-10}$M). The retinoid examples cited do not have a limiting character.

The SPSEC profiles are obtained after incubation of the F9 cells with $2 \times 10^{-9}$M of the compound of example 1 in the absence (♦-♦) or in the presence of $10^{-9}$M(□-□), $10^{-8}$M (■-■), $10^{-7}$M (Δ-Δ), $10^{-6}$M (▲-▲) of cold competitors. I=the unmarked compound of example 1. RA=retinoic acid. The inhibition sigmoids given in boxes enabled the determination of the IC50 given in Table 1. For each competition concentration, the peak surface is expressed as a percentage of the surface obtained with the compound of example 1 without competition.

By measuring the surface of the radioactive peak for each concentration of cold competition, it is possible to trace the competition sigmoids. Data processing of these curves enables the determination of the IC50 (50% inhibiting concentration) of each retinoid. As a control, the IC50 of cold compound I was also measured and a biologically inactive retinoid (compound VIII) was also used. Table 1 shows the values of IC50 obtained It can be noted that compound I has an affinity for the RARs which is six times better than that of retinoic acid itself.

Correlation between the biological activity of retinoids and their affinity for the RARs as determined by competition using the compound of example 1

The biological activity of the retinoids can be measured on the F9 cells by quantifying the production of the plasminogen activator secreted consecutively with the differentiation of said cells, caused by the retinoids. CPA50 is the concentration of retinoids causing an induction of 50% of the maximum of the secreted plasminogen activator. By comparing the IC50 and CPA50 values on Table 1, it can be noted that there is an excellent correlation between the affinity of the retinoids for the RARs and their biological activity (see also the straight regression line of FIG. 4). The only exception is retinoic acid itself. This fact is explained by the high instability of this product. In effect, the IC50 measurement is carried out after an incubation of 3 hours, while the CPA50 measurement is carried out after a incubation of 3 days.

Figure 4:
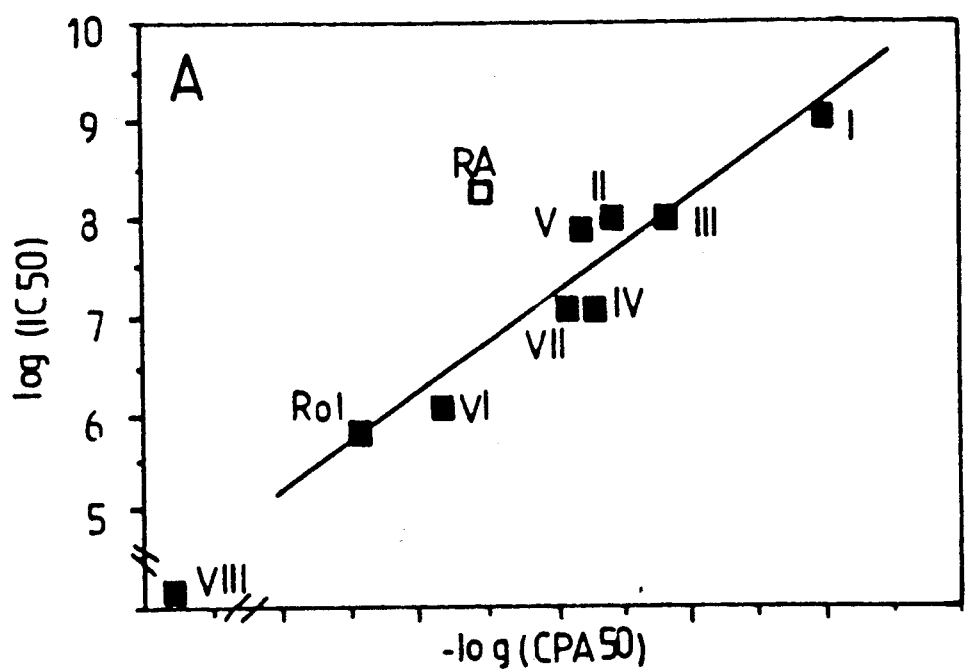
FIG. 4 represents the linear regression between the biological retinoids, retinol, retinoic acid, compounds I, II, III, IV, V, VI and VIII and their affinity for RARs.

FIG. 4 represents the linear regression showing an excellent correlation between the biological activity of retinoids (CPA50) and their affinity for the RARs. The values corresponding to retinoic acid (RA=□) have not been used. The affinity for the RARs and the biological activity of compound VIII are below the threshold of detection.

Characteristics of fixing the compound of example 1 on the CRABP binding protein The results relating to the fixing of compound I and retinoic acid on CRABP are shown in FIG. 5. The direct fixing of increasing concentrations of the compound of example 1 (b) and retinoic acid (a) to rat testicle cytosol containing CRABP in the absence (●-●) or in the presence of 1000 nM of cold homolog ligand was studied. The difference (■-■) represents the specific bond.

The fixing of the claimed compound on CRABP has been characterized by saturation experiments (see FIG. 5b). The total fixing (non-specific + specific (1-1) is obtained by incubation of increasing concentrations (up to a maximum of 125 nM) of the claimed compound with a constant quantity (0.3 ml) of a rat testicle homogenate (CRABP-rich organ). The non-specific fixing of the tritiated compound is determined in parallel, by measuring the fixing with increasing concentrations of the radioactive ligand in the presence of a large excess (1 µM) of cold homolog ligand (□-□). An incubation time of two hours is necessary for the establishment of balanced conditions.

Once the balance is achieved, the tritiated CRABP-ligand complex is separated from the non-bonded ligand by filtration on a Sephadex G25 exclusion gel column (BIO-Rad econo columns, 0.5 × 20 cm): the complex is eluted (elution peak at 2.5 ml), while the non-bonded ligand is retained in totality on the column. The result is total separation between the bonded and non-bonded product. The elution is done directly in scintillation tubes and the radioactivity is measured by counting.

The results obtained in this manner were analyzed by non-linear regression using the Clark equation as a model (A. J. Clark, The mode of action of drugs on cells; A. Arnold and Co., London, 1933).

The abscissa on FIG. 1 represent the initial concentrations of the ligand studied, and the ordinates represent the concentrations with the balance of the ligand-binding protein complex.

The difference between the total fixing curve (●-●) and the non-specific fixing curve (□-□) gives the specific fixing curve (■-■). Analysis of this curve provides the dissociation constant with the balance (Kd), which is the concentration of product necessary to saturate 50% of the CRABP. This constant is a measurement of the affinity of the ligand for its binding protein, with the Kd being inversely proportional to the affinity (the lower the Kd, the greater the affinity).

This analysis gives a Kd value of 4 nM. The specific fixing is saturable and reversible. The non-specific fixing is linear and non-saturable in the range of concentrations used, and represents less than 10% of the total fixing. The concentration of CRABP in the rat testicle cytosol used for the experiment can be determined in binding experiments where the marked retinoids are used at a saturating concentration. A value of 10–12 pmol/mg protein is found both with the claimed compound and with the retinoic acid. On the other hand, using HPSEC it can be determined that these two ligands are fixed on a molecule with a molecular weight of 15 kDa (molecular weight of the CRABP) with the same elution profile.

Comparison with tritiated retinoic acid

Under these same conditions, the fixing of retinoic acid on CRABP can be studied (FIG. 5a). The Kd value of the retinoic acid is 2 nM, with the non-specific fixing representing approximately 25% of the total fixing.

Determination of the affinity of a retinoic for CRABP by competition with the claimed marked compound These competition experiments are carried out in the following manner: a fixed quantity of radioactive ligand (corresponding substantially to the demi-saturation, in our case 4 nM) is mixed with increasing quantities of cold ligand (non-radioactive). Then the binding protein is added and the quantity of radioactive ligand fixed to the balance is determined (in % of the initial fixing in the absence of cold ligand, for the quantity of CRABP under consideration).

From the competition curves, the IC50 (concentration of cold ligand reducing the attachment of the tritiated ligand by 50%) is determined. This IC50 value enables the calculation in each case of the dissociation constant from the balance (Kd) for the cold ligand.

Table 1 indicates the values which were determined for the various compounds studies. Identical values were determined if, instead of the claimed compound, marked retinoic acid itself was used in the competition experiments.

TABLE 1

| Comparison of the biological activity of retinoids and of their affinity for the RARs and CRABP | | | |
|---|---|---|---|
| | BIOLOGICAL ACTIVITY CPA50 (nM) | AFFINITY | |
| | | RARs:IC50 (nM) | CRABP:Kd (nM) |
| Retinoic acid | 350 | 5 | 2 |
| Retinol | 2,500 | 1,400 | 600 |
| Compound I | 1 | 0.8 | 4 |
| Comopund IV | 53 | 77 | 2 |
| Compound V | 66 | 12 | 20 |
| Compound VI | 670 | 770 | 200 |
| Compound VII | 85 | 76 | 200 |
| Compound VIII | >10,000 | >10,000 | 200 |

NB:
Compound I = cold compound of example 1 (unmarked)
Compound IV = 2-(5,6,7,8-tetrahydro-5,5,8,8-tetramethyl-2-naphthyl)-6-benzo(b)-thiophene carboxylic acid
Compound V = 6-(5,6,7,8-tetrahydro-5,5,8,8-tetramethyl-2-naphthyl)-2-naphthoic acid
Compound VI = 2-(5,6,7,8-tetrahydro-5,5,8,8-tetramethyl-2-naphthyl)-6 benzo(b-)furan carboxylic acid
Compound VII = 4-(5,6,7,8-tetrahydro-5,5,8,8-tetramethyl-2-naphthamido) benzoic acid
Compound VIII = 1-methyl-4-thiol-6-(5,6,7,8-tetrahydro-5,5,8,8-tetramethyl-2-naphthyl)-2-naphthoic acid

We claim:
1. 4-(5,6,7,8-tetrahydro-5,5,8,8-tetramethyl-2-anthracenyl) benzoic acid labelled with tritium.
2. The tritiated 4-(5,6,7,8-tetrahydro-5,5,8,8-tetramethyl-2-anthracenyl) benzoic acid of claim 1 having a specific activity of at least 1875 GBq/mmole.

* * * * *